United States Patent
Lorsch (10) Patent No.: US 8,775,212 B2
(45) Date of Patent: Jul. 8, 2014

(54) ELECTRONIC HEALTH RECORDS IN CLINICAL TRIALS

(75) Inventor: Robert H. Lorsch, Los Angeles, CA (US)

(73) Assignee: Mymedicalrecords, Inc, Los Angeles, CA (US)

(*) Notice: Subject to any disclaimer, the term of this patent is extended or adjusted under 35 U.S.C. 154(b) by 92 days.

(21) Appl. No.: 13/082,896

(22) Filed: Apr. 8, 2011

(65) Prior Publication Data

US 2011/0251855 A1  Oct. 13, 2011

Related U.S. Application Data

(60) Provisional application No. 61/322,649, filed on Apr. 9, 2010.

(51) Int. Cl.
| | |
|---|---|
| *G06Q 50/00* | (2012.01) |
| *G06F 19/00* | (2011.01) |
| *A61B 5/00* | (2006.01) |
| *G06Q 50/24* | (2012.01) |

(52) U.S. Cl.
CPC ............ *G06F 19/322* (2013.01); *G06F 19/363* (2013.01); *G06Q 50/24* (2013.01)
USPC .................................................. 705/3; 705/2

(58) Field of Classification Search
CPC ....... G06Q 50/22; G06Q 50/24; G06F 19/363
USPC ......................................................... 705/2–3
See application file for complete search history.

(56) References Cited

U.S. PATENT DOCUMENTS

| | | | |
|---|---|---|---|
| 6,651,060 B1 | 11/2003 | Harper et al. | |
| 7,251,609 B1 | 7/2007 | McAlindon et al. | |
| 7,428,494 B2 | 9/2008 | Hasan et al. | |
| 7,440,904 B2 | 10/2008 | Hasan et al. | |
| 7,475,020 B2 | 1/2009 | Hasan et al. | |
| 7,509,264 B2 | 3/2009 | Hasan et al. | |
| 7,533,030 B2 | 5/2009 | Hasan et al. | |
| 7,707,047 B2 | 4/2010 | Hasan et al. | |
| 7,720,691 B2 | 5/2010 | Hasan et al. | |
| 8,131,563 B2 | 3/2012 | Hasan et al. | |
| 2002/0143563 A1* | 10/2002 | Hufford et al. | 705/1 |
| 2003/0033168 A1* | 2/2003 | Califano et al. | 705/3 |
| 2003/0140044 A1* | 7/2003 | Mok et al. | 707/10 |

(Continued)

OTHER PUBLICATIONS

Griffin, The Textbook of Pharmaceutical Medicine, 2009, Wiley, 6th Edition, p. 215.*

(Continued)

*Primary Examiner* — Joy Chng (74) *Attorney, Agent, or Firm* — McKee, Voorhees & Sease (57) ABSTRACT

A method for collecting self-reported data from an individual for use in a clinical trial is provided. The method includes providing a web site allowing the individual to store, organize, and access personal health records associated with the individual and sharing selected personal health records associated with the individual with a clinical trial sponsor. A system for electronic health records includes a web server programmed to provide a secure web-based interface to the electronic health records, means to collect self-reports from an individual participating in a clinical trial, means to disseminate the self-reports from the individual to a clinical trial sponsor, and means to collect health care records from a health care provider of the individual.

16 Claims, 6 Drawing Sheets

(56) References Cited

U.S. PATENT DOCUMENTS

| | | | |
|---|---|---|---|
| 2003/0208378 A1* | 11/2003 | Thangaraj et al. | 705/2 |
| 2004/0078216 A1* | 4/2004 | Toto | 705/2 |
| 2004/0093240 A1* | 5/2004 | Shah | 705/2 |
| 2004/0102683 A1* | 5/2004 | Khanuja et al. | 600/300 |
| 2004/0172447 A1* | 9/2004 | Miller | 709/203 |
| 2005/0075909 A1* | 4/2005 | Flagstad | 705/3 |
| 2007/0067189 A1 | 3/2007 | Boris et al. | |
| 2008/0010254 A1 | 1/2008 | Settimi | |
| 2008/0086337 A1 | 4/2008 | Soon-Shiong | |
| 2008/0133270 A1 | 6/2008 | Michelson et al. | |
| 2009/0055222 A1 | 2/2009 | Lorsch | |
| 2009/0083703 A1 | 3/2009 | Grady et al. | |
| 2009/0313045 A1 | 12/2009 | Boyce | |

OTHER PUBLICATIONS

Cronin, Personal Health Records: An Overview of What Is Available to the Public, Apr. 2006, AARP, 23 pages.*

Griffin, The Textbook of Pharmaceutical Medicine, 2009, Wiley, 6th Edition, p. 215.*

Mymedicalrecords.com, Inc., International Search Report, PCT/US11/31772 dated Jun. 16, 2011, 2 pages.

Baker, Toni, "Impact of electronic personal health record on hypertension under study" Feb. 6, 2008 MCG News, 4 pages; https://my.mcg.edu/portal/page/portal/News/archive/2008/Impact%20of%20electronic%20 . . . printed off Internet on Apr. 13, 2010.

EHR Clinical Research Value Case Workgroup, "Value Case for the Use of Electronic Health Records in Clinical Research: Processes to Support core Research Data Element Exchange" 17 pages (Apr. 2009).

Marchionini, Gary et al., "Evidence Base for Personal health Record Usability final Report to the National Cancer Institute" Univeristy of North Carolina at chapel Hill, Feb. 10, 2007, 33 pages.

Perkins, Richard, "Electronic health Records for Clinical Research" "EHR Compliant to Clinical Trial Requirements", EuroRec Conference 2009, 22 page presentation.

Raymond, Stephen A. et al., "Electronic Subject Diaries in Clinical Trials", Applied Clinical Trials, www.phtcorp.com, Mar. 2000, 8 pages.

"Tele-Diab: Electronic diary for Patients With Type 2 diabetes mellitus", http:/www.clincialtrials.gov/ct2/show/nct01058889, printed from Internet on Apr. 11, 2011, 1 page.

"Clinical Trials Compliance Triples With Electronic Diaries" http://www.crfhealth.com/news_press_release.php?id=36, Jun. 8, 2008. CRF Health Real Patient Data 24/7. 2 pages.

Market Research.com "Electronic Patient Diaries: Driving Clinical R&D and Post-Launch Marketing Efforts" published Aug. 13, 2002, 3 pages.

PDA Cortex: The largest Selection of Medical & Nursing PDA Software, "The Journal of Mobile Informatics" http://www.pdacortex.com printed from Internet on Apr. 11, 2011, 3 pages.

"ePRO-Electronic Patient Diary system for Clinical Trials" "Make the Most of Every Patient", http://www.phtcorp.com, printed from Internet on Apr. 11, 2011, 1 page.

* cited by examiner

ELECTRONIC HEALTH RECORDS IN CLINICAL TRIALS

CROSS-REFERENCE TO RELATED APPLICATIONS

This application claims priority under 35 U.S.C. §119 to provisional application Ser. No. 61/322,649 filed Apr. 9, 2010, herein incorporated by reference in its entirety.

FIELD OF THE INVENTION

The present invention relates to electronic health records. More particularly, but not exclusively, the present invention relates to the use of personal health records in clinical research.

BACKGROUND OF THE INVENTION

There are numerous problems associated with clinical trials. One problem relates to patient compliance issues. As part of a trial, patients may be required to self-report data. The type of data may vary considerably dependent upon the particular protocols of the clinical trial. Examples of such data may include when medication were taken, whether exercises were performed, level of pain being experienced, etc. However, even conscientious participant in a clinical trial may find it difficult to comply with reporting requirements. Patient compliance issues are significant because these issues can potentially affect the validity or results of a clinical trial or study. Thus, patient compliance problems may potentially change the outcome of a clinical trial study, such as causing a safe and effective pharmaceutical or treatment to fail to receive approval, or to create gaps in the understanding of a particular pharmaceutical or treatment.

Various attempts have been made at addressing these problems. One example of such an approach is for a participant to use a diary or electronic diary to record self-reporting information. Yet, there are still problems with such an approach. Clinical trial participants may find it difficult or inconvenient to record information whether in a diary or electronic diary or may forget to record the information periodically, or may attempt to reconstruct the information too long after the fact to be accurate.

In addition to these issues with diaries and electronic diaries, such systems are limited in functionality. What is needed are systems and methods which integrate self-reports of participants in clinical studies with other medical information associated with the patient and which allow the patient to selectively disseminate that information, including to clinical trial sponsors.

BRIEF SUMMARY OF THE INVENTION

Therefore, it is a primary object, feature, or advantage of the present invention to improve over the state of the art.

It is a further object, feature, or advantage of the present invention to improve the effectiveness of clinical trials.

It is a still further object, feature, or advantage of the present invention to reduce the cost of clinical trials.

It is a further object, feature, or advantage of the present invention to provide a benefit to science and society.

Yet another object, feature, or advantage of the present invention is to save lives.

Another object, feature, or advantage of the present invention is to provide more accurate data on the effectiveness of drugs and treatment therapies.

Yet another object, feature, or advantage of the present invention is to improve patient compliance in clinical trials.

A still further object, feature, or advantage of the present invention is to alert emergency responders of a patient's participation in a clinical trial at the time that emergency care is given.

Another object, feature, or advantage of the present invention is to remind individuals when to take their medication.

Yet another object, feature, or advantage of the present invention is to confirm that an individual took their medication.

Another object, feature, or advantage of the present invention is to provide an electronic diary for use by patients in a clinical trial which merges information associated with the clinical trial into the patient's personal health record.

Yet another object, feature, or advantage of the present invention is to improve efficiency in collecting and reporting self-reported patient data.

A still further object, feature, or advantage of the present invention is to reduce time to market for pharmaceuticals and treatment therapies.

Another object, feature, or advantage of the present invention is to provide selective access to emergency information, including information on the participation of an individual in a clinical trial or study.

Another object, feature, or advantage of the present invention is to provide a private communications link between healthcare personnel and their patients as well a private communications link between a clinical trial sponsor and an individual.

A still further object, feature, or advantage of the present invention is to facilitate storing all of an individual or family's medical records and related information in a single location so that healthcare personnel can be given complete medical information/history when needed or analysis can be performed on the medical records.

Yet another object, feature, or advantage of the present invention is to give users the ability to forward records via fax to a healthcare provider.

A further object, feature, or advantage of the present invention is to give users the ability to see if there are any possible interactions between prescription drugs they are taking.

Yet another object, feature, or advantage of the present invention is to allow for the healthcare provider to quickly and easily, yet securely, communicate records associated with an individual to the individual.

A still further object, feature, or advantage is to provide a web site for management of health care records which is modular in design, to allow for additional features and functions to be integrated easily and rapidly.

Another object, feature, or advantage of the present invention is to provide a web site for management of health care records that allows health-care related content from any number of sources to be displayed on the web site.

Yet another object, feature, or advantage of the present invention is to provide a web site for management of health care records that integrates with other web sites such as by providing the ability to do a single sign-on on a related web site (authentication, authorization, and accounting) and then provide access to the web site for management of health care records.

A still further object, feature, or advantage of the present invention is to assist emergency health care providers in verifying that records they acquire match the patient in need of emergency assistance.

Yet another object, feature, or advantage of the present invention is to share patient generated data with an electronic medical record.

A further object, feature, or advantage of the present invention is to share Electronic Medical Record generated data with patient data.

One or more of these and/or other objects, features, and advantages of the present invention will become apparent from the specification and claims that follow. No single embodiment need exhibit each and every of these objects, features, or advantages. The present invention is not to be limited to or by these objects, features, and advantages.

According to one aspect of the present invention, a method for collecting self-reported data from an individual for use in a clinical trial is provided. The method includes providing a web site allowing the individual to store, organize, and access personal health records associated with the individual and sharing selected personal health records associated with the individual with a clinical trial sponsor. The selected personal health records may be specified by the individual through the web site.

According to another aspect of the present invention, a system for electronic health records is provided. The system includes a web server programmed to provide a secure web-based interface to the electronic health records through a first web portal, means to collect self-reports from an individual participating in a clinical trial and communicate the self-reports to the first web portal, means to disseminate the self-reports from the individual to a clinical trial sponsor, and means to collect health care records from a health care provider of the individual and communicate the health care records to the first web portal. The first portal may be configured to provide access to both the self-reports and the health care records to the individual to the individual.

According to another aspect of the present invention, a method for assisting in conducting a clinical trial is provided. The method includes providing participants in the clinical trial with access to a first web portal. The method further includes receiving self-reports from the participants in the clinical trial via at least one of phone, fax, and web and storing the self-reports and making available the self-reports to the participants through the first web portal. The method further includes receiving additional medical records associated with the participants from the participants in the clinical trial or health care providers of the participants in the clinical trial and making available the medical records to the participants through the first web portal. The method further includes providing a clinical trial sponsor with access to a second web portal, the self-reports from the participants in the clinical trial being made available through the second web portal. The method further includes selectively providing the additional medical records to the clinical trial sponsor according to preferences of the participants.

DETAILED DESCRIPTION OF THE PREFERRED EMBODIMENTS

Figure 1:
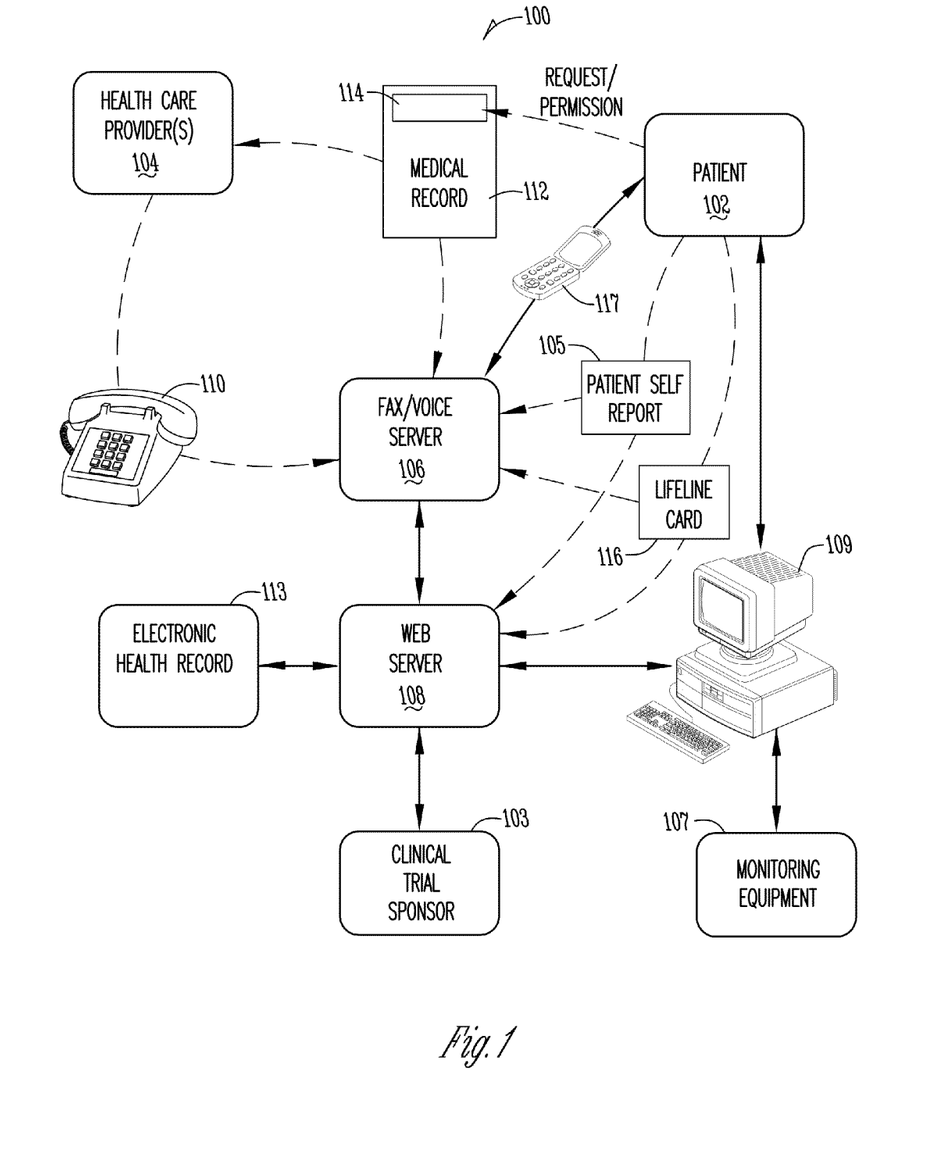
FIG. 1 is a diagram illustrating one embodiment of a system for collecting medical records, collecting self-reported personal health information, and disseminating relevant self-reported personal health information to a clinical trial sponsor.

FIG. 1 is a diagram illustrating one embodiment of a system 100 of the present invention. In FIG. 1, a person or patient 102 is shown. A clinical trial sponsor 103 is also shown. For purposes herein the term "clinical trial sponsor" is intended to include contract research organizations or others for, with, or on behalf of the clinical trial sponsor regardless of the specific legal relationship. A fax/voice server 106 is shown as well as a web server 108.

As part of a pharmaceutical or therapy trial (or otherwise), the patient 102 can communicate a patient self-report 105. The patient self-report 105 may take any one or more of numerous forms. For example, completion of the patient self-report may involve completing a paper form. The paper form may include a number of ovals which are filled out, boxes which are checked, blanks for entering information, or may be of other formats. The paper form may also include one or more bar codes with information identifying the patient or information associated with the clinical trial. Where a paper form is used, the paper form may be faxed to the fax/voice server 106. An image representation of the paper form may be stored on the web server 108 or otherwise. Optical character recognition or related processes may be performed to collect data from the image of the paper form which in turn may be used to create an electronic health record 113. In addition, the data collected may be communicated to a clinical trial sponsor 103.

The patient self-report 105 may take on other forms. For example, the fax/voice server 106 which may also perform interactive voice response (IVR) functions, may periodically call the patient 102 or may receive a call from the patient 102 using the phone 117. The patient 102 may then be presented with questions regarding their health condition, their compliance with the requirements of the pharmaceutical or therapy trial, or other questions designed to provide useful feedback to the clinical trial sponsor 103. Information obtained from the self-report in this manner may also be used to create an electronic health record 113 which may be stored on the web server 108 and/or made available to the clinical trial sponsor 103.

The specific information collected will vary based on the protocols of the specific clinical trial. Examples of self-reported data may include, without limitation, whether medications were taken or no, the amount of medication taken, the time of day that medication was taken, whether exercise was performed, a description of the type or amount of exercise performed, data about food or liquid intake, data about general well-being, or other information.

Another form of the patient self-report 105 is an online electronic form. The patient 102 may use a computer 109 to communicate with the web server 108 in order to provide the self-report 105. Information obtained from the self-report 105 may also be used to create an electronic health record 113 which may be stored on the web server 108 and/or made available to the clinical trial sponsor 103.

Another form of the patient self-report 105 is through text messaging. The patient may use a phone 117 to send a self-report to the fax/voice server 106. The self-report may be in response to text messages from the fax/server 106 asking for specific self-reporting information. Information obtained from the self-report via text messages may also be used to create an electronic health record 113 which may be stored on the web server 108 and/or made available to the clinical trial sponsor 103.

Yet another form of the patient self-report 105 is through email messages. The patient may use the computer 109 or phone 117 or other device to send a self-report in an email or in response to an email.

It is also contemplated that the patient need not use only a single method for providing the self-report. It is contemplated that the patient may use a combination of voice, text message, fax, and online self-reports. It is further contemplated that for any particular study or trial that multiple types of self-reporting may be used by patients. The ease of self-reporting simplified the patient's participation in the study or clinical trial as well as allowing the data to be collected quickly and efficiently. In addition, the self-report form a part of the electronic health record 113 of the patient 102 which may provide the patient 102 and health care provider(s) 104 with valuable and important electronic health records which may assist in providing health care to the patient.

The system 100 also provides for increasing compliance with the terms of a study or clinical trial by contacting the patient 102 to remind the patient 102 of the need to comply with self-reporting requirements. For example, the fax/voice server 106 may send a SMS or other type of text message to the phone 117 of the patient 102 or a pager of the patient 102. Alternatively, an email message may be sent to the patient 102. Alternatively, the fax/voice server or system with IVR functionality may call the patient 102 to remind them of the need to self-report. Where the self-report 105 may be made using voice, the user may then immediately provide the self-report.

The system 100 may also collect information associated with monitoring equipment 107. Various types of medical monitoring equipment may be used by the patient 102 which is capable of acquiring data regarding the patient 102. Data collected by the monitoring equipment may be communicated to the computer 109 and from the computer 109 to the web server 108. Alternatively, such data may be communicated directly to the web server 108 or otherwise communicated to the web server 108. Data from the monitoring equipment 107 may be used to create electronic health records 113. The present invention contemplates that in some clinical trials, the patient 102 will be required to consent to monitoring by the monitoring equipment and reporting the data to the clinical trial sponsor 103.

The present invention further contemplates that where monitoring equipment 107 is used, if data acquired is indicative of a health issue, the system may generate an alert to the patient 102 and/or physician or nurse or healthcare professional indicating that the patient 102 should seek immediate medical care, such as from their health care provider(s) 104 or otherwise. In addition, if agreed to by the patient 102, the alerts can be sent directly to the health care provider. The alerts may be sent through the voice server (such as through an IVR subsystem), via email, via text message, or otherwise.

The system 100 may provide for collecting and storing medical records associated with the patient 102, not merely the electronic health records created through self-reports associated with the participation of the patient 102 in a clinical trial. Thus, a healthcare provider 104 is also shown. The healthcare provider 104 uses the phone 110 to communicate private voicemail messages through a phone number to the fax/voice server 106. The phone number may, but need not be, a dedicated phone number, or a toll-free dedicated phone number.

In addition, the healthcare provider faxes health or medical records 112 to the fax/voice server 106 using the phone number. The medical record 112 preferably has a sticker 114 present on the medical record 112 or a file folder associated with the individual. The sticker 114 indicates or instructs the healthcare provider 104 or their staff to fax the information to the phone number. In addition, the sticker 114 provides an indication of clear consent from the patient 102 to the healthcare provider 104 to the phone number. Thus, it becomes a simple process for a consumer or patient 102 to provide their healthcare provider 104 with instructions to fax health records, a simple process for the healthcare provider 104 to obtain permission to fulfill a request for healthcare records, and a simple process for the healthcare provider 104 to do so in a secure and convenient manner as the fax is going directly to the phone number associated with the patient 102.

The web server 108 is operatively connected to the fax/voice server 106 such as over a network or otherwise. A patient 102 or their proxy can communicate directly with the web server 108 through a computing device 109 or the fax/voice server 106 using a phone 117. The patient 102 can use a LIFELINE card 116 that contains access information to log on to the web server 108 associated with a web site of the present invention, or as a reminder of their phone number which they can call to access voicemail messages, listen to text-to-speech conversion of emails, or otherwise access information.

The present invention also allows a patient 102 to upload files using a computing device 109 to the web server 108. These files may include self-reports associated with a study or clinical trial in which the patient 102 participates. In addition, the patient 102 can use the computing device 109 to interact with the web server 108 to specify that a prescription or other personal health record is faxed via the fax/voice server 106 to a healthcare provider 104 or to the clinical trial sponsor 103. In addition, other types of electronic health records may be imported from other systems. For example, GoogleHealth records previously created by the patient 102 may be imported.

The present invention also allows a physician or other health care provider to communicate health information to the web server 108. Such information may be provided directly such as by uploading or emailing or otherwise electronically communicating an electronic health record 113 to the web server 108. Thus, the present invention allows for records from the health care provider to be added to the system regardless of whether their records are paper-based or electronic.

Figure 2:
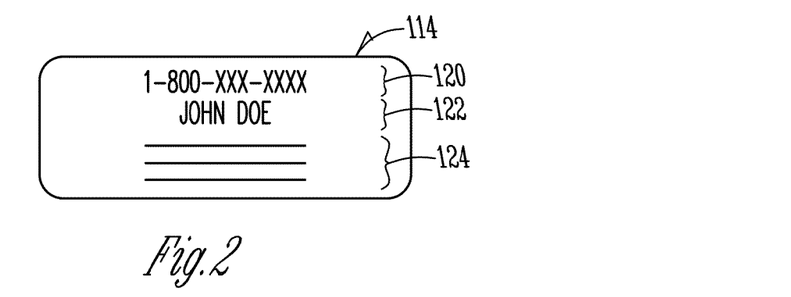
FIG. 2 is a pictorial representation of a sticker authorizing transmissions of records to the user account according to one embodiment of the present invention.

FIG. 2 illustrates one embodiment of a sticker 114 for a patient to give to their healthcare provider to request or instruct their healthcare provider to fax, phone, or email medical records to the patient. For fax and phone the medical records may be sent to a toll free dedicated phone number associated with the patient. Although it is preferred that a sticker 114 be used because of the added convenience provided by being able to permanently or semi-permanently attach to a patient file at a healthcare providers office, the present invention contemplates that other types of documents could be used. The sticker 114 includes the LIFELINE phone number 120 which is the phone number associated with the patient. Note that in one embodiment, there is no pin number required which greatly simplifies the process of faxing documents. In addition, the name 122 of the patient is shown. There is also a written request 124 on the sticker 114 that instructs the healthcare provider to fax the records and explicitly gives permission to fax the healthcare record. The language of the written request 124 may vary as necessary to comply with any applicable laws. It should be appreciated that the sticker 114 provides great convenience to both an individual who wants to instruct their healthcare provider to give them access to their medical records as well as to the healthcare provider who can now easily provide the individual with access to their medical records. The present invention further contemplates that medical alert information can also be placed on the sticker 114. The types of medical alert information includes, without limitation, blood type information (i.e. ABO and Rhesus information), allergies to drugs, presence of a pacemaker, diabetes, epilepsy, or other conditions. In addition, alert information may include clinical trial participation information. The clinical trial participation information may include the name of the clinical trial, contact information regarding the clinical trial, or other information associated with the clinical trial.

Figure 3A:
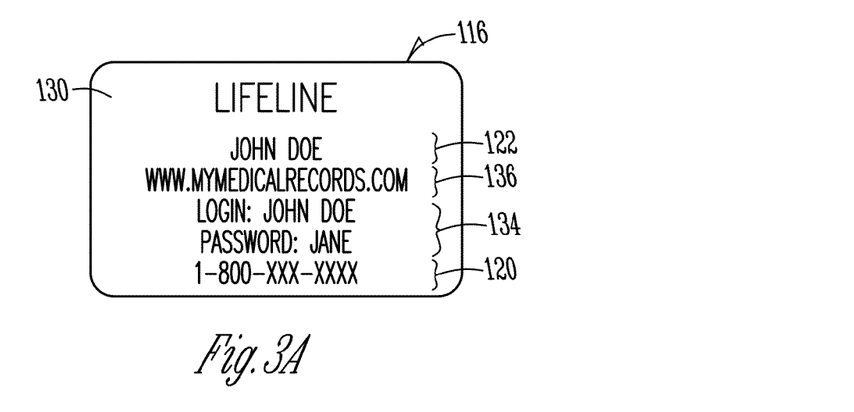
FIG. 3A and FIG. 3B illustrate a card with medical record access information and which indicates participation within a clinical trial.
Figure 3B:
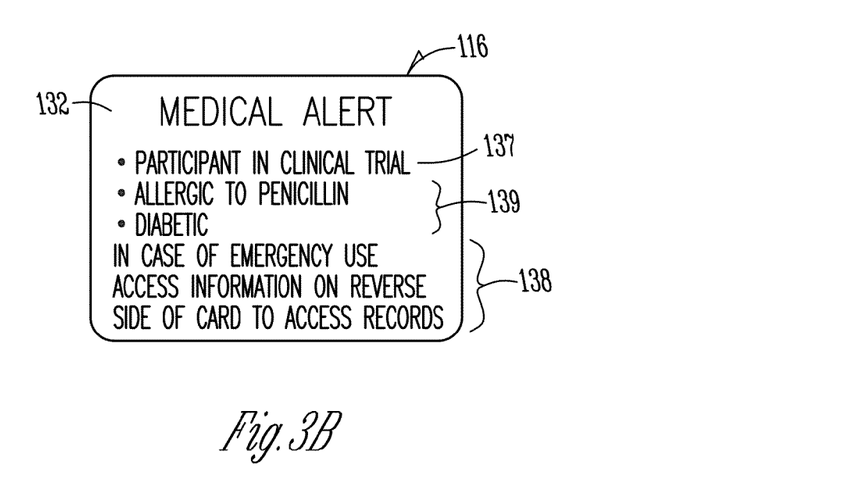

FIG. 3A and FIG. 3B illustrate one embodiment of a LIFELINE card 116. The LIFELINE card has a front side 130 and an opposite back side 132. The card 116 includes the name of the individual 122, a URL for a web site 136 which stores medical records for the individual. In addition there is access information 134 such a username and password. The card 116 also includes the phone number 120 associated with the individual. On the back side 132 of the card 116 as best shown in FIG. 3B, medical alert information 139 is provided. The medical alert information 139 can include allergies which the individual has, medical conditions such as diabetes or epilepsy, the presence of a pacemaker, or other medical information that may be of great importance in evaluating or treating the individual in the case of a medical emergency. The medical alert information can further include blood type information (i.e. ABO and Rhesus information). Also, instructions 138 are provided on the card 116 to indicate how one could access complete medical records or information about the individual. In addition, alert information may include clinical trial participation information 137. The clinical trial participation information may include the name of the clinical trial, contact information regarding the clinical trial, a URL associated with the clinical trial, or other information associated with the clinical trial.

Figure 4:
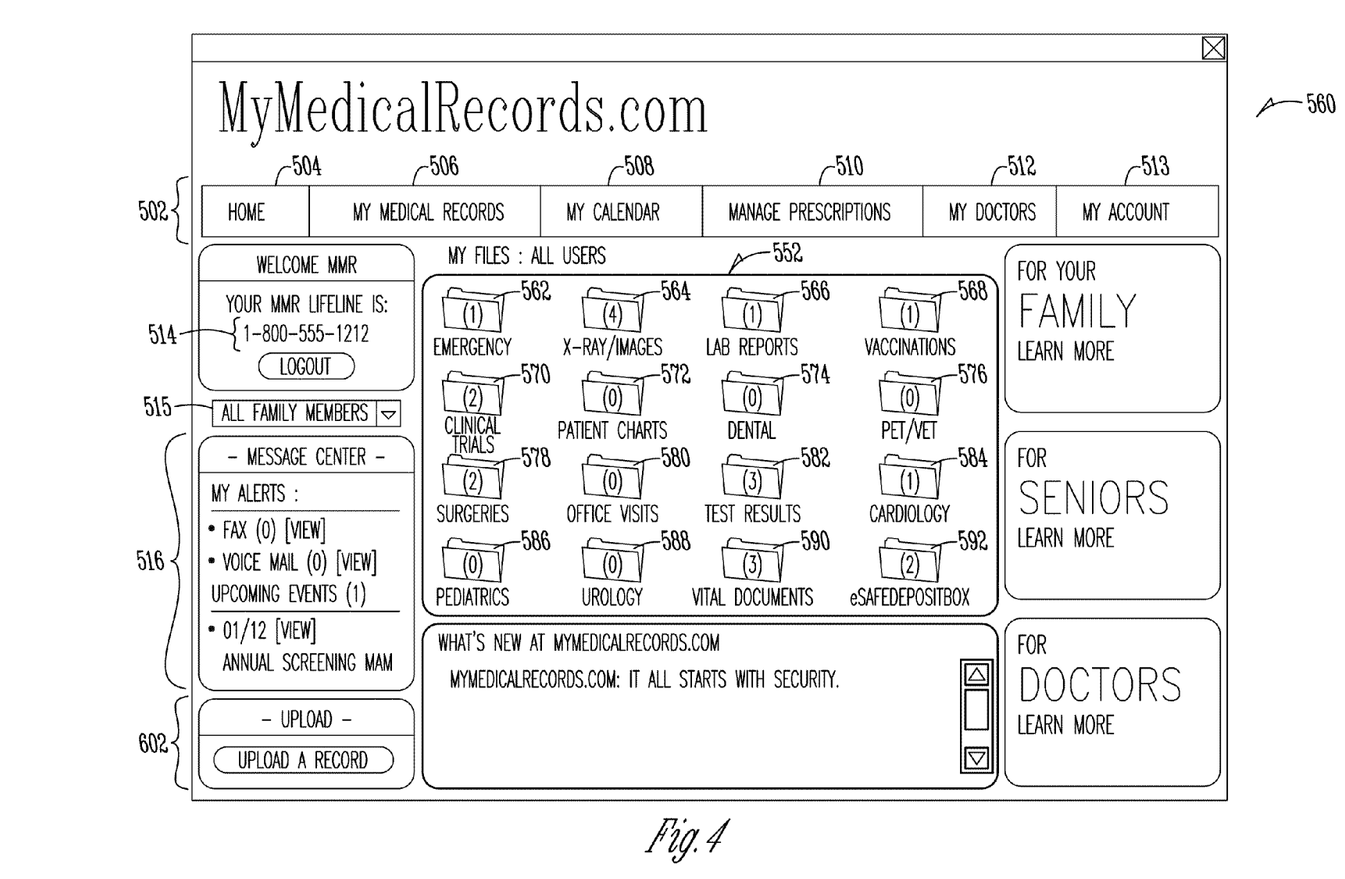
FIG. 4 is an example of a screen display associated with a web site for collecting, organizing, and disseminating health records.

FIG. 4 is an example of a screen display 560 according to one embodiment of the present invention. FIG. 4 shows tabs 502 for HOME 504, MY MEDICAL RECORDS 506, MY CALENDAR 508, MANAGE PRESCRIPTIONS 510, MY DOCTORS 512, and MY ACCOUNT 513. A phone number 514 is shown and a MESSAGE CENTER 516 is shown. Note that a MYACCOUNT option 513 is shown near the top of the screen display 560. Also note that a user is allowed to select a family member using the dropdown list box 515. There is also an upload record option 602 provided so that a user may upload files of various types directly to their account.

Shown in the MY FILES portion 552 are a plurality of file folders, including: EMERGENCY folder 562, X-RAY/IMAGES folder 564, LAB REPORTS 566, VACCINATIONS 568, CLINICAL TRIALS 570, PATIENT CHARTS 572, DENTAL 574, PET/VET 576, SURGERIES 578, OFFICE VISITS 580, TEST RESULTS 582, CARDIOLOGY 584, PEDIATRICS 586, UROLOGY 588, VITAL DOCUMENTS 590, eSAFEDEPOSITBOX 592. The various file folders shown provide a convenient method for users to organize their files. Note that each folder indicates how many files are stored within the file folder.

Note that electronic health records associated with a clinical trial may be stored in the CLINICAL TRIALS folder 570. Thus, electronic health records created by any number of means of self-reporting, including through voice, fax, web, email, texting or otherwise, may be placed in the clinical trials folder 570 upon creation. In addition electronic health records relevant to the clinical trial but created by a manner other than self-reporting may also be included in the CLINICAL TRIALS folder 570. Should a patient be involved in more than one clinical trial, there may be multiple clinical trial folders.

The present invention allows for the user to specify that self-reports be placed directly in the CLINICAL TRIALS folder 570 so that the user does not need to move the self-reports to the folder 570. In addition, self-reports may be communicated to the clinical trial sponsor. Alternatively, or additionally, the user may give the clinical trial sponsor access to the CLINICAL TRIALS folder 570. Thus, the clinical trial sponsor may access the self-reports as well as any other information that the user places in the folder 570. It is contemplated that different clinical trials may have different requirements regarding data collection and health record sharing and thus, depending upon the conditions of a particular clinical trial or study, participants may need to place different types of data in the CLINICAL TRIALS folder 570. The participants in the clinical trial would provide informed consent to allow for any sharing of data.

It should further be appreciated that the present invention also facilitates easy sharing of information. In addition to information which a patient may be required to submit as a requirement to their participation in a clinical trial, the patient may choose to share other information. This can be performed in various ways such as by moving documentation to the CLINICAL TRIALS folder 570. Thus, an individual can share selected personal health records associated with the individual with a clinical trial sponsor, wherein the selected personal health records are specified by the individual through the web site such as by moving those records to the CLINICAL TRIALS folder 570 and/or allowing the individual to specify that the self-reports be placed directly in the CLINICAL TRIALS folder 570.

The present invention provides for each of the file folders to be protected with one or more additional passwords. Such an implementation is particularly useful in a number of contexts. For example, the use of multiple passwords allows information such as insurance information, legal information, financial information, or other proprietary information to be protected differently than the medical records. Similarly, such an implementation allows for different types of security for different types of medical records, should the user so desire. Another example of where this extra layer of security can be useful is where a single account is shared by a family consisting of two parents and multiple children. Each parent may have their own folder separately password protected so that the other parent cannot access their folder, but still allowing both parents to access the folders for the children.

Figure 5:
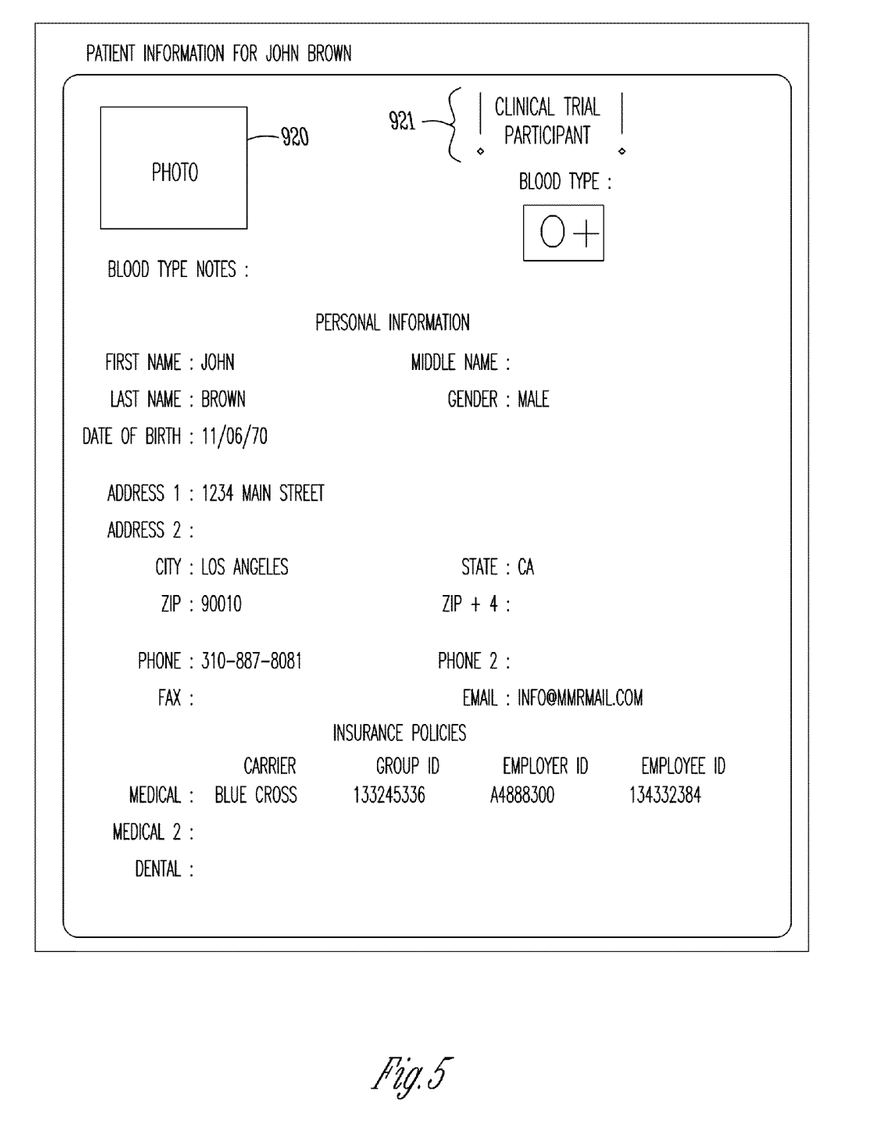
FIG. 5 and FIG. 6 illustrate one embodiment of the most critical information and records which are provided in case of an emergency, including participation within a clinical trial.
Figure 6:
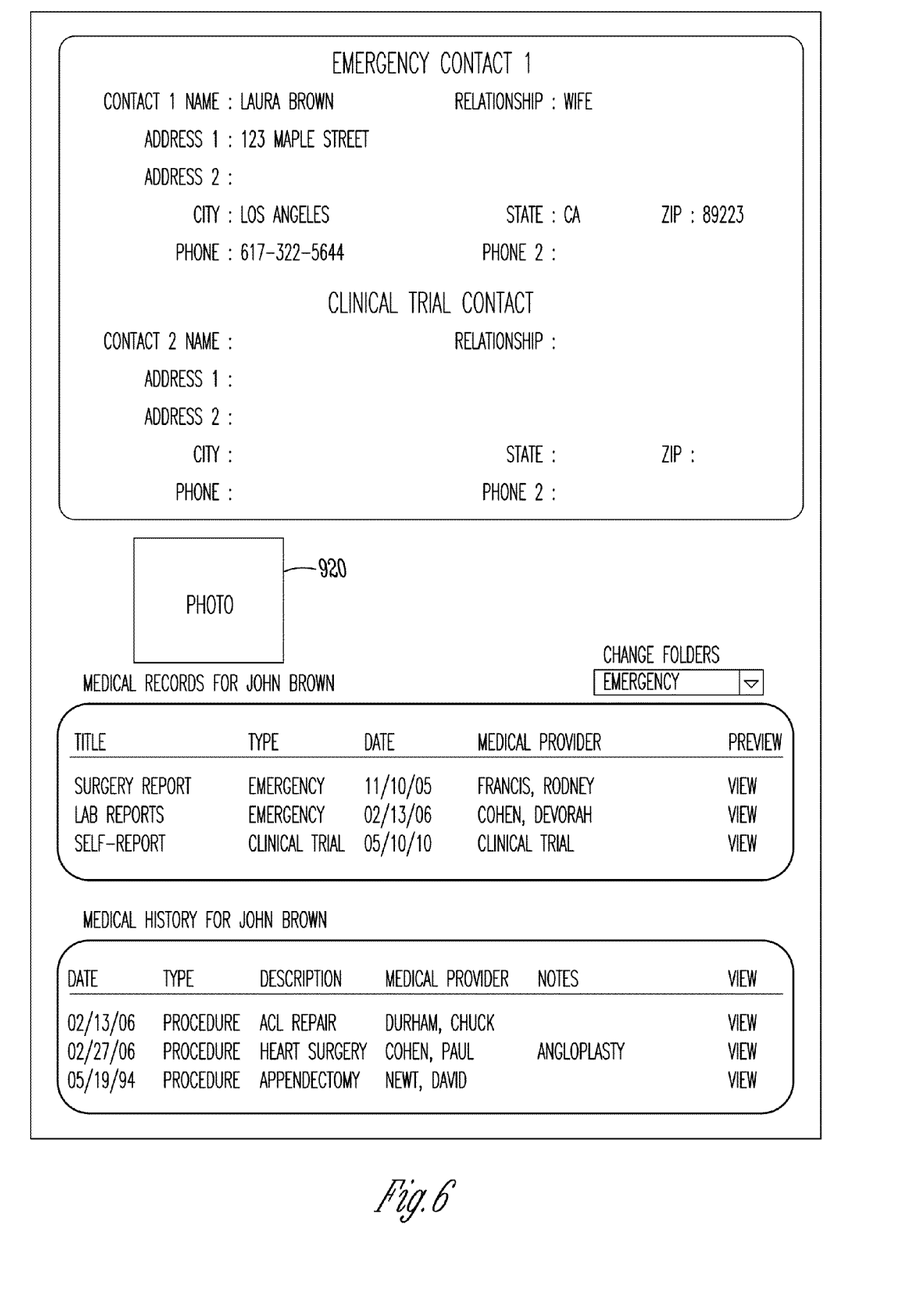

FIG. 5 and FIG. 6 illustrate one embodiment of the most critical information and records which are provided in case of an emergency. Additional information can be accessed from this screen. Note also that in both FIG. 5 and FIG. 6, a photo 920 of the individual may be shown. Having the photo 920 readily available helps first responders or other emergency care providers to verify that they have correctly matched the emergency card with the correct individual, if no one is able to confirm identity of the individual. In addition, note that in FIG. 5, an alert 921 indicates that the patient is a clinical trial participant. In FIG. 6, contact information associated with a clinical trial may also be provided. Thus, the clinical trial sponsor may be contacted after an emergency to alert the clinical trial sponsor. It is completed that the contact information may be associated with doctor or other health care provider associated with the clinical trial.

If there is a concern that the emergency was somehow related to the clinical trial, then the clinical trial sponsor may immediately begin to analyze or evaluate the circumstances, alert other clinical trial participants of potential risks, or selectively alert other clinical trial participants that may have risks. In addition, after being advised of the emergency, the reminders to self-report may be temporarily suspended.

Also in FIG. 6, self-reports made in conjunction with a clinical trial may be made available to emergency health care personnel. Information obtained in the self-reports may be valuable for diagnosis reasons and providing a more complete history of the patient than would normally be available without the self-reporting associated with a clinical.

Figure 7:
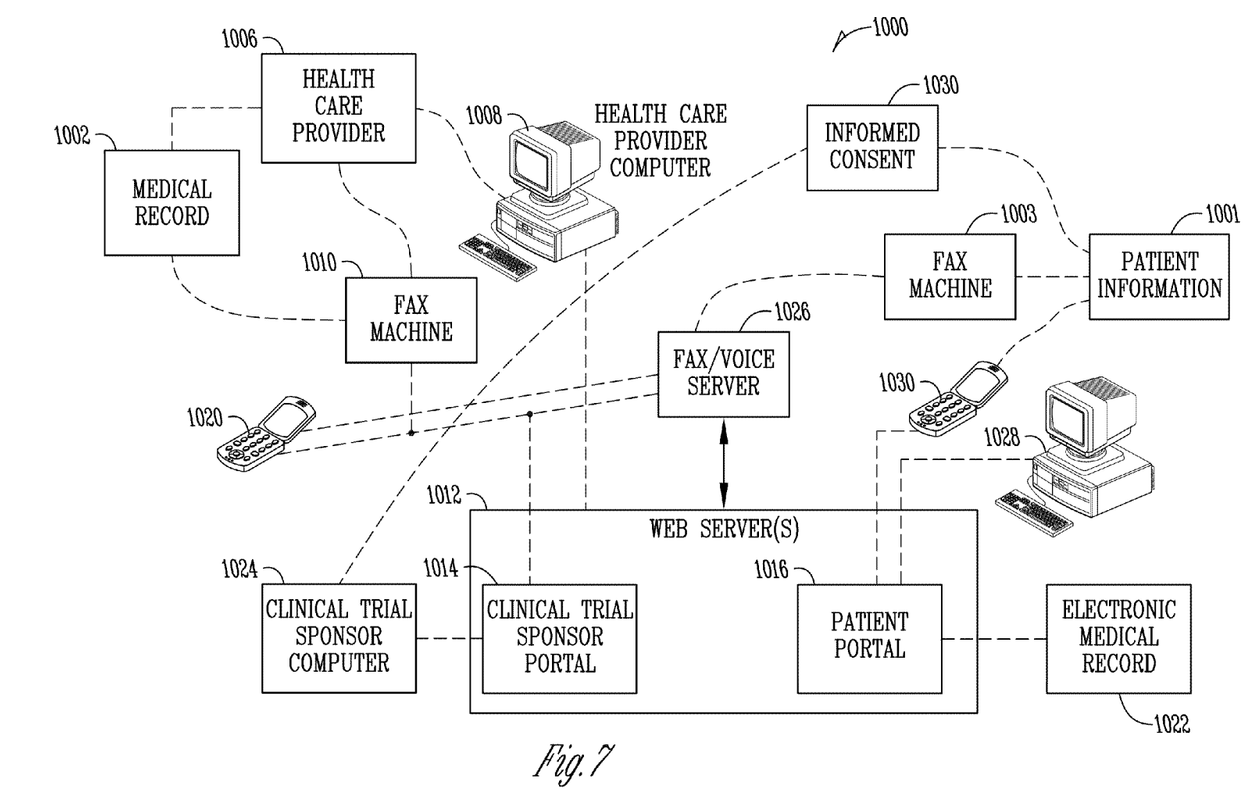
FIG. 7 illustrates one example of a system which provides for collection of medical records from health care providers, the collection of self-reported data from patients or clinical trial participants and the dissemination of relevant records such as to clinical trial sponsors, where appropriate informed consent is obtained.

FIG. 7 illustrates one example of a system 1000. The system 1000 allows for the collection of medical records from health care providers, the collection of self-reported data from patients or clinical trial participants. The system 1000 makes available the medical records and self-reported data to the patient. In addition, the system 1000 allows clinical trial sponsors to access the data collected as a part of the clinical trial, while preventing access to data which the patient desires to keep private.

In FIG. 7, a patient 1001 may use a fax machine 1003, phone 1030, computer 1028, or other device to communicate with the fax/voice server 1026 and/or the web server(s) 1012. In this way, the patient 1001 may provide for self-reporting which becomes part of electronic medical records, as well as accessing their own medical records (and other types of stored records), organizing their medical records, and disseminating their medical records to health care providers, clinical trial sponsors, or others.

The web server(s) 1012 may include a clinical trial sponsor portal 1014 as well as a patient portal 1016. Thus, the clinical trial sponsor 1024 may also be able to access the web server(s) 1012 to store and organize records, download compilations of records or other activities that assist in conducting the clinical trial. The present invention contemplates that the clinical trial sponsor portal 1014 may provide additional functionality as well. This can include analysis of the records being collected.

The system also allows health care providers such as health care provider 1006 to fax (such as using fax machine 1010 in communication with fax/voice server 1026) or electronically communicate medical records through health care provider computer 1008 to the web server(s) 1012. Similarly, the health care provider 1006 may communicate voice messages using phone 1020 to the fax/voice server 1026. The system 1000 also allows for the creation of electronic medical records 1022 which may be disseminated to health care provider 1006 or otherwise.

An informed consent document 1030 is also shown which is associated with a clinical trial. The informed consent document 1030 may specify the data which the patient/clinical trial participant 1001 agrees to share as a part of their participation in the clinical trial. This may include the self-reported data of the patient as well as other relevant health information.

As should also be apparent from FIG. 7, documents, emails, files, and images (including medical images such as x-rays and scans) may be uploaded by the patient, by the health care provider or otherwise.

The present invention provides a number of advantages both to clinical trial sponsors, participants in clinical trials, health care providers who provide health care services to participants in clinical trials, and to society at large.

In particular, the system address compliance issues with clinical trials in several ways. First, the system allows for multiple types of contact with clinical trial participants. This encourages and guides the participation within a clinical trial. Thus data can be collected from the participants nearer the time of the event underlying the data which serves to increase the reliability of the data. In addition, once collected, the data can be made available to the clinical trial sponsor immediately. In addition, other health or medical information of the participant may be made available to the clinical trial sponsor which may assist in evaluation of pharmaceuticals or treatments under study. In addition, by having clinical trial sponsor contact information associated with emergency contacts, the clinical trial sponsor may be made aware of emergency events and thus potentially provide information of assistance in diagnosis or treatment of the patient, or to evaluate whether the occurrence of the emergency event is indicative of any special risks to other participants in the clinical trial. If such a special risk is identified and communication with clinical trial participants is needed, the system allows for patients to be contacted in various ways so that clinical trial participants can be contacted as quickly as possible.

Thus, the systems and methods described assist in improving the effectiveness of clinical trials, reducing the cost of clinical trials, providing accurate data on the effectiveness of drugs and treatment therapies, and other data.

The systems and methods also provide various potential advantages to patients/clinical trial participants. The system increases the convenience with any self-reporting associated with a clinical trial by allowing communication to take various forms. In addition, the system allows for the creation of personal health records based on self-reporting data, thereby allowing individuals to better document their health. In addition, the system allows for providing patients with a convenient way to collect medical records from health care providers and to disseminate this information to clinical trial sponsors or others, while still being in control of their records and deciding what information to share.

The system also provides a convenient and effective way for health care providers 1006 to provide medical records to their patients. In addition, the system allows for building more complete histories of patients which may increase or enhance a health care provider's ability to provide proper patient care.

It should be apparent that the present invention may be used in a variety of contexts. This includes collection of data in various phases of clinical trials as well as post-marketing.

Thus, various methods and systems related to electronic health records in clinical trials has been described. Although specific embodiments have been provided, the present invention is not to be limited to these embodiments, as the present invention contemplates numerous variations, options, and alternatives.

The invention claimed is:

1. A method for collecting self-reported data from an individual for use in a clinical trial, the method comprising:
   providing a web site stored on a web server, the web site enabling the individual to store, organize, and access health records associated with the individual on the web site, the web site further configured to collect the health records by:
   (a) receiving self-reports from the individual and creating electronic health records from the self-reports, (b) receiving data from medical monitoring equipment for acquiring data indicative of a health issue of the individual and creating electronic health records from the data, and (c) receiving health records from a health care provider of the individual;

collecting the health records at the web site, the collecting the health records comprising (a) receiving the self-reports from the individual and creating the electronic health records from the self-reports, (b) receiving the data from the medical monitoring equipment indicative of a health issue of the individual and creating the electronic health records from the data, and (c) receiving the health records from the health care provider of the individual;

storing the health records on a computer readable storage medium associated with the web site; and sharing selected health records associated with the individual with a clinical trial sponsor through a clinical trial portal, wherein the selected health records are specified by the individual through the web site;

providing a wallet card comprising emergency information associated with the individual including an emergency password and a web site identifier associated with the web site;

making available through the web site at least a subset of the health records in event of emergency through the emergency information; and making available through the web site clinical trial participation information in event of the emergency through the emergency information.

2. The method of claim 1 wherein the receiving the self-reports comprises receiving the self-reports at a fax server in operative communication with the web server.

3. The method of claim 2 where the receiving the self-reports comprises receiving the self-reports through an interactive voice response system of a server.

4. The method of claim 1 wherein the receiving the self-reports comprises receiving the self-reports through the web site.

5. The method of claim 1 wherein the self-reports include bar codes.

6. The method of claim 1 wherein the receiving the self-reports comprises receiving the self-reports via text messages from a phone.

7. A system for electronic health records, comprising:

a web server programmed to provide a secure web-based interface to the electronic health records through a first web portal;

means to collect self-reports from an individual participating in a clinical trial and self-reporting by sending text message from a phone and communicate the self-reports to the first web portal;

means to disseminate the self-reports from the individual to a clinical trial sponsor; and means to collect health care records from a health care provider of the individual and communicate the health care records to the first web portal;

means to receive medical monitoring equipment data from medical monitoring equipment for acquiring data indicative of a health issue of the individual and create electronic health records from the medical monitoring equipment data from the medical monitoring equipment;

wherein the first web portal being configured to provide access to the self-reports, the medical monitoring equipment data from the medical monitoring equipment, and the health care records to the individual.

8. The system of claim 7 wherein the web server being programmed to provide emergency access to data of the individual through use of an emergency log-on to the first web portal; wherein the data of the individual includes clinical trial contact information; wherein the data includes self-reports associated with the clinical trial; wherein the data includes data selected by the individual for the emergency access; and wherein emergency log-on instructions being provided on an emergency card.

9. The system of claim 7 wherein the first web portal allows the individual having access through the first web portal to specify health care records to share with the clinical trial sponsor.

10. A method for assisting in conducting a clinical trial, the method comprising:

providing participants in the clinical trial with access to a first web portal associated with a web server;

receiving self-reports from the participants in the clinical trial via text messages from phones and storing the self-reports in a computer readable storage medium and making available the self-reports to the participants through the first web portal associated with the web server;

receiving additional medical records associated with the participants from the participants in the clinical trial or health care providers of the participants in the clinical trial and making available the medical records to the participants through the first web portal;

receiving medical monitoring equipment data associated with the participants from medical monitoring equipment for acquiring data indicative of a health issue of the participants;

sending a reminder to the participants to remind the participants of the need to comply with self-reporting requirements, wherein the reminder comprises a text message, a voice message, an email, a phone call, and/or any combination of the foregoing;

providing a clinical trial sponsor with access to a second web portal, the self-reports from the participants in the clinical trial being made available through the second web portal;

selectively providing the additional medical records to the clinical trial sponsor according to preferences of the participants; and selectively providing the medical monitoring equipment data to the clinical trial sponsor according to preferences of the participants.

11. A method for collecting self-reported data from an individual, the method comprising:

providing a web site stored on a web server, the web site enabling the individual to store, organize, and access health records associated with the individual on the web site, the web site further configured to collect the health records by:

(a) receiving self-reports from the individual and creating electronic health records from the self-reports, (b) receiving data from medical monitoring equipment for acquiring data indicative of a health issue of the individual and creating electronic health records from the data, and (c) receiving health records from a health care provider of the individual;

receiving a self-report from the individual via text message from a phone;

creating an electronic health record using the self-report from the individual;

storing the electronic health record on the web site;

receiving data from medical monitoring equipment indicative of a health issue of the individual;

creating an electronic health record using the received data from medical monitoring equipment;

storing the electronic health record on the web site receiving an additional health record from a health care provider for the individual at the web site;

storing the additional health record from the health care provider on the web site;

sharing selected health records on the web site as specified by the individual through the web site.

12. The method of claim 11 wherein the sharing the selected health records on the web site as specified by the individual through the web site further comprises sharing the selected health records on the web site as specified by the individual through the web site with a clinical trial sponsor.

13. The method of claim 12 wherein the clinical trial sponsor accesses the selected health records through a clinical trial sponsor portal.

14. A method for collecting self-reported data from an individual, the method comprising:

providing a web site stored on a web server, the web site enabling the individual to store, organize, and access personal health records associated with the individual on the web site, the web site further configured to collect the health records by:

(a) receiving self-reports from the individual and creating electronic health records from the self-reports, (b) receiving data from medical monitoring equipment associated with the individual and creating electronic health records from the data, and (c) receiving health records from a health care provider of the individual;

receiving data from the medical monitoring equipment indicative of a health issue of the individual at the web site;

creating an electronic health record from the data from the medical monitoring equipment;

storing the electronic health record on a computer readable storage medium associated with the web site;

sharing selected health records associated with the individual as specified by the individual through the web site;

programming the web server to provide emergency access to clinical trial data of the individual through use of an emergency log-on to a first web portal using an additional password designated for emergencies; and wherein the clinical trial data of the individual includes clinical trial contact information, self-reports associated with the clinical trial, and data selected by the individual for the emergency access.

15. The method of claim 14 wherein the sharing the selected health records on the web site as specified by the individual through the web site further comprises sharing the selected health records on the web site as specified by the individual through the web site with a clinical trial sponsor.

16. The method of claim 15 wherein the clinical trial sponsor accesses the selected health records through a clinical trial sponsor portal.

* * * * *